United States Patent [19]

Connor et al.

[11] 4,404,138

[45] Sep. 13, 1983

[54] 3-[2-(AZABICYCLO)ETHYL]-1,2,3,4-TETRAHYDRO-5H-[1]BENZOPYRANO[3,4-C]PYRIDIN-5-ONES

[75] Inventors: David T. Connor, Ann Arbor; Charles F. Schwender, Dexter; Roderick J. Sorenson; Paul C. Unangst, both of Ann Arbor, all of Mich.

[73] Assignee: Warner-Lambert Company, Morris Plains, N.J.

[21] Appl. No.: 391,197

[22] Filed: Jun. 22, 1982

[51] Int. Cl.$^3$ .................................. C07D 491/052
[52] U.S. Cl. .................................. 260/244.4; 546/62; 546/65; 546/89; 546/92; 424/256
[58] Field of Search ............... 546/62, 65, 89, 92; 424/256; 260/244.4

[56] References Cited

U.S. PATENT DOCUMENTS 3,661,919  5/1972  Razdan et al. ............... 546/89 X
3,689,497  9/1972  Brown et al. ............... 546/92
3,914,237  10/1975  Pars et al. ............... 546/89 X
3,946,008  3/1976  Brown et al. ............... 546/92 X
3,991,196  11/1976  Brown et al. ............... 546/89 X
4,013,671  3/1977  Brown et al. ............... 546/89 X
4,018,766  4/1977  Brown et al. ............... 546/89 X
4,117,140  9/1978  Brown et al. ............... 546/92 X
4,276,296  6/1981  Brown et al. ............... 546/92 X Primary Examiner—Donald G. Daus
Assistant Examiner—William A. Teoli, Jr.
Attorney, Agent, or Firm—Jerry F. Janssen

[57] ABSTRACT

Anticholinergic 3-[2-(azabicyclo)ethyl]-1,2,3,4-tetrahydro-5H-[1]benzopyrano[3,4-c]pyridin-5-ones useful for treating bronchospastic diseases in mammals are disclosed. Also disclosed are methods for preparing said compounds, pharmaceutical compositions containing them and methods for using said pharmaceutical compositions.

19 Claims, No Drawings

3-[2-(AZABICYCLO)ETHYL]-1,2,3,4-TETRAHYDRO-5H-[1]BENZOPYRANO[3,4-c]PYRIDIN-5-ONES

BACKGROUND OF THE INVENTION

The compounds of the invention are 3-[2-(azabicyclo)ethyl]-1,2,3,4-tetrahydro-5H-[1]benzopyrano[3,4-c]pyridin-5-ones which have anticholinergic activity. The compounds are useful as bronchodilators.

U.S. Pat. No. 4,276,296 discloses anticholinergic 3-[2-(1-pyrrolidinyl and 1-piperidinyl)propyl]1,2,3,4-tetrahydro-5H-[1]benzopyrano[3,4-c]pyridin-5-ones.

SUMMARY OF THE INVENTION

The invention sought to be patented in its generic chemical compound aspect is a compound having the structural formula I

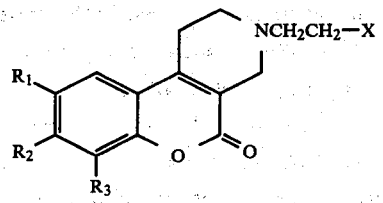

wherein
$R_1$ is H, alkyl of from 1 to 6 carbon atoms, alkoxy of from 1 to 6 carbon atoms, hydroxy, nitro, halo, amino, or acylamino;
$R_2$ is H, hydroxy, alkyl of from 1 to 6 carbon atoms, alkoxy of from 1 to 6 carbon atoms or phenyl;
$R_3$ is H, or alkoxy of from 1 to 6 carbon atoms;
$R_1$ and $R_2$ taken together are $OCH_2O$;
$R_2$ and $R_3$ taken together are $CH=CH-CH=CH$;
X is

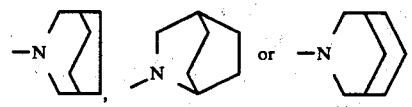

and the pharmaceutically acceptable salts thereof, provided that $R_1$ is not hydroxy when $R_2$ is $OC_2H_5$ and X is

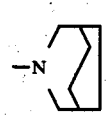

The invention sought to be patented in a first subgeneric chemical compound aspect is a compound having structural formula I wherein $R_3$ is H; and the pharmaceutically acceptable salts thereof.

The invention sought to be patented in a second subgeneric chemical compound aspect is a compound having structural formula I wherein X is

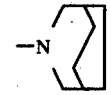

and the pharmaceutically acceptable salts thereof.

The invention sought to be patented in a first specific chemical compound aspect is the compound having the name 3-[2-(3-azabicyclo[3.2.2]non-3-yl)ethyl]-8-ethyl-1,2,3,4-tetrahydro-5H-[1]benzopyrano[3,4-c]pyridin-5-one and the pharmaceutically acceptable salts thereof.

The invention sought to be patented in a second specified chemical compound aspect is the compound having the name 3-[2-(3-azabicyclo[3.2.2]non-3-yl)ethyl]-8-(1,1-dimethylethyl)-1,2,3,4-tetrahydro-5H-[1]benzopyrano[3,4-c]pyridin-5-one and the pharmaceutically acceptable salts thereof.

The invention sought to be patented in a third specific chemical compound aspect is the compound having the name 3-[2-(3-azabicyclo[3.2.2]non-3-yl)ethyl]-1,2,3,4-tetrahydro-8-methoxy-5H-[1]benzopyrano[3,4-c]pyridin-5-one and the pharmaceutically acceptable salts thereof.

The invention sought to be patented in a fourth specific chemical compound aspect is the compound having the name 3-[2-(3-azabicyclo[3.2.2]non-3-yl)ethyl]-1,2,3,4-tetrahydro-8-hydroxy-5H-[1]benzopyrano[3,4-c]pyridin5-one and the pharmaceutically acceptable salts thereof.

The invention sought to be patented in a fifth specific chemical compound aspect is the compound having the name 3-[2-(3-azabicyclo[3.2.2]non-3-yl)ethyl]-1,2,3,4-tetrahydro-8,9-diethoxy-5H-[1]benzopyrano[3,4-c]pyridin-5-one and the pharmaceutically acceptable salts thereof.

The invention sought to be patented in a sixth specific chemical compound aspect is the compound having the name 3-[2-(2-azabicyclo[2.2.2]oct-2-yl)ethyl]-1,2,3,4-tetrahydro-8-methoxy-5H-[1]benzopyrano[3,4-c]pyridin-5-one and the pharmaceutically acceptable salts thereof.

The invention sought to be patented in a seventh specific chemical compound aspect is the compound having the name 3-[2-(2-azabicyclo[2.2.2]oct-2-yl)ethyl]-1,2,3,4-tetrahydro-8,9-dimethoxy-5H-[1]benzopyrano[3,4-c]pyridin-5-one and the pharmaceutically acceptable salts thereof.

The invention sought to be patented in an eighth specific chemical compound aspect is the compound having the name 3-[2-(3-azabicyclo[3.3.1]non-3-yl)ethyl]-1,2,3,4-tetrahydro-8,9-dimethoxy-5H-[1]benzopyrano[3,4-c]pyridin-5-one and the pharmaceutically acceptable salts thereof.

The invention sought to be patented in a ninth specific chemical compound aspect is the compound having the name 3-[2-(3-azabicyclo[3.3.1]non-3-yl)ethyl]-1,2,3,4-tetrahydro-8-methoxy-5H-[1]benzopyrano[3,4-c]pyridin-5-one and the pharmaceutically acceptable salts thereof.

The invention sought to be patented in a tenth specific chemical compound aspect is the compound having the name 3-[2-(3-azabicyclo[3.2.2]non-3-yl)ethyl]-1,2,3,4-tetrahydro-8-,9-dimethoxy-5H-[1]benzopyrano[3,4-c]pyridin-5-one and the pharmaceutically acceptable salts thereof.

The invention sought to be patented in a eleventh specific chemical compound aspect is the compound having the name 3-[2-(3-azabicyclo[3.2.2]non-3-yl)ethyl]-1,2,3,4-tetrahydro-8,9-dimethyl-5H-[1]benzopyrano[3,4-c]pyridin-5-one and the pharmaceutically acceptable salts thereof.

The invention sought to be patented in an twelfth specific chemical compound aspect is the compound having the name 3-[2-(3-azabicyclo[3.2.2]non-3-yl)ethyl]-1,2,3,4-tetrahydro-8,-(1-methylethyl)-5H-[1]benzopyrano[3,4-c]pyridin-5-one and the pharmaceutically acceptable salts thereof.

The invention sought to be patented in a thirteenth specific chemical compound aspect is the compound having the name N-{3-[2-(3-azabicyclo[3.2.2]non-3-yl)ethyl]-1,2,3,4-tetrahydro-8-methyl-5-oxo-2H-[1]benzopyrano[3,4-c]pyridin-9-yl}-acetamide and the pharmaceutically acceptable salts thereof.

The invention sought to patented in a fourteenth specific chemical compound aspect is the compound having the name 3-[2-(2-azabicyclo(3.2.2]non-3-yl)ethyl-1,2,3,4-tetrahydro-5H-[1]benzopyrano[3,4-c]pyridin-5-one and the pharmaceutically acceptable salts thereof.

The invention sought to be patented in its chemical process aspect is a process for preparing a chemical compound having structural formula I which comprises reacting a compound having structural formula II with a compound having the formula hal-CH$_2$CH$_2$-X. The invention sought to be patented in its pharmaceutical composition aspect is a composition consisting essentially of a compound having structural formula I in combination with a pharmaceutically acceptable carrier.

The invention sought to be patented in its pharmaceutical method aspect is a method for treating asthma or bronchitis in a mammal in need of such treatment, which comprises administering an effective amount of the above defined pharmaceutical composition to said mammal.

DESCRIPTION OF THE PREFERRED EMBODIMENTS

The compounds of the invention having structural formula I

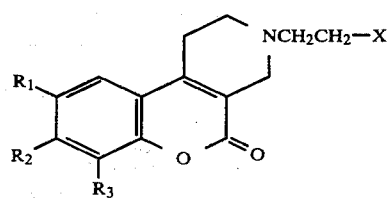

prepared by different procedures which are considered equivalent for purposes of the invention. One such procedure involves the reaction of a compound of structural formula II with a compound of the formula

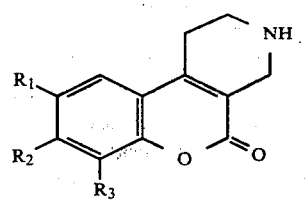

Hal—CH$_2$CH$_2$—X. The term Hal, represents chlorine, bromine, or iodine and is preferably chlorine.

This reaction proceeds most conveniently by contacting compound II and the compound Hal—CH$_2$CH$_2$—X in a convenient nonreactive solvent in the presence of a hydrogen halide acceptor such as a tertiary amine, pyridine or an inorganic metal carbonate or bicarbonate. Useful solvents are alcohols such as ethanol and the like. Useful hydrogen halide acceptors are triethylamine, pyridine, sodium bicarbonate, potassium carbonate, and the like.

The compounds of structural formula II are prepared by condensing a properly substituted phenol having structural formula III with 4-oxo-3-piperidine-carboxylic acid, IV.

III

R$_1$
R$_2$
R$_3$
OH

This condensation is conveniently performed in concentrated sulfuric acid (preferably about 75% H$_2$SO$_4$) utilizing IV in the form of its methyl ester, hydrochloride, which is commercially available (e.g. from Aldrich Chemical Co., Milwaukee, Wis. 53201, USA). The phenols of structural formula III are either commercially available or may be prepared by conventional procedures known to those skilled in the art.

The intermediate of structural formula II wherein R$_1$=R$_2$=R$_3$=H (II′) is disclosed in British Pat. No. 1,455,522 example 2. The synthetic method described therein reports a 10% yield, but could not be consistently reproduced. This compound was successfully prepared according to the following reaction sequence.

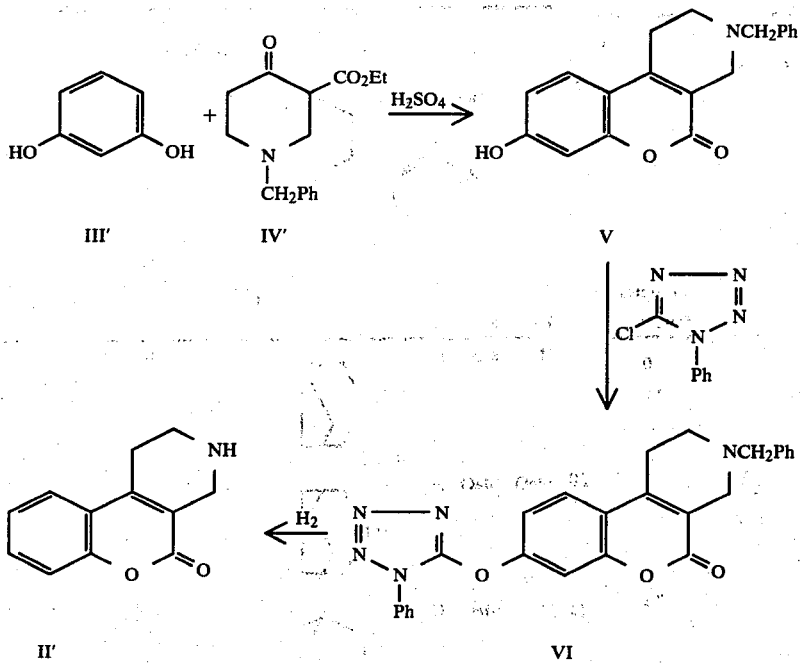

The condensation between resorcinol (III') and 1-benzyl-3-carbethoxy-4-piperidone (IV') to produce compound V is carried out in ca. 75% sulfuric acid. The compound IV' may be prepared as described in Beilstein 22 (2) 216. Those skilled in the art will recognize that other carbalkoxy groups may be present at the 3-position of IV' and that the same product V will thereby be produced. Carbethoxy is preferrred. The reaction between V and 5-chloro-1-phenyl-1H-tetrazole [Beilstein 26 (2) 197] is carried out in a convenient nonreactive solvent such as dimethylformamide or dimethylsulfoxide in the presence of an acid acceptor such as sodium carbonate, potassium carbonate, and the like. This reaction proceeds efficiently at a temperature of about 70°–100° C. and is substantially complete in about 3 to about 10 hours. Compound IV is converted to II' by reaction with elemental hydrogen using standard procedures. For example, the reaction proceeds efficiently at room temperature in acetic acid at about 50 lbs/in² hydrogen pressure in the presence of 20% Pd/C. The reaction is complete when hydrogen uptake ceases.

The compounds of the invention display anticholinergic properties when tested by the following procedure:

Conscious guinea pigs, six at a time, are put into a sealed chamber and exposed for 10 minutes to an aerosol of methacholine. Untreated animals or those treated with vehicle will collapse in 1.9±0.1 minutes. Groups of animals are injected intraperitoneally with 25 mg/kg of test compound and exposed in the chamber under the same conditions. Compounds which prolong the collapse time past that of the control animals are considered active. Activity in this procedure indicates that the compound would be of use in treating those bronchospastic diseases such as asthma and bronchitis which have a high degree of cholinergic-mediated vagal tone.

Utilizing the above test procedure, the following results were obtained for representative compounds of the invention.

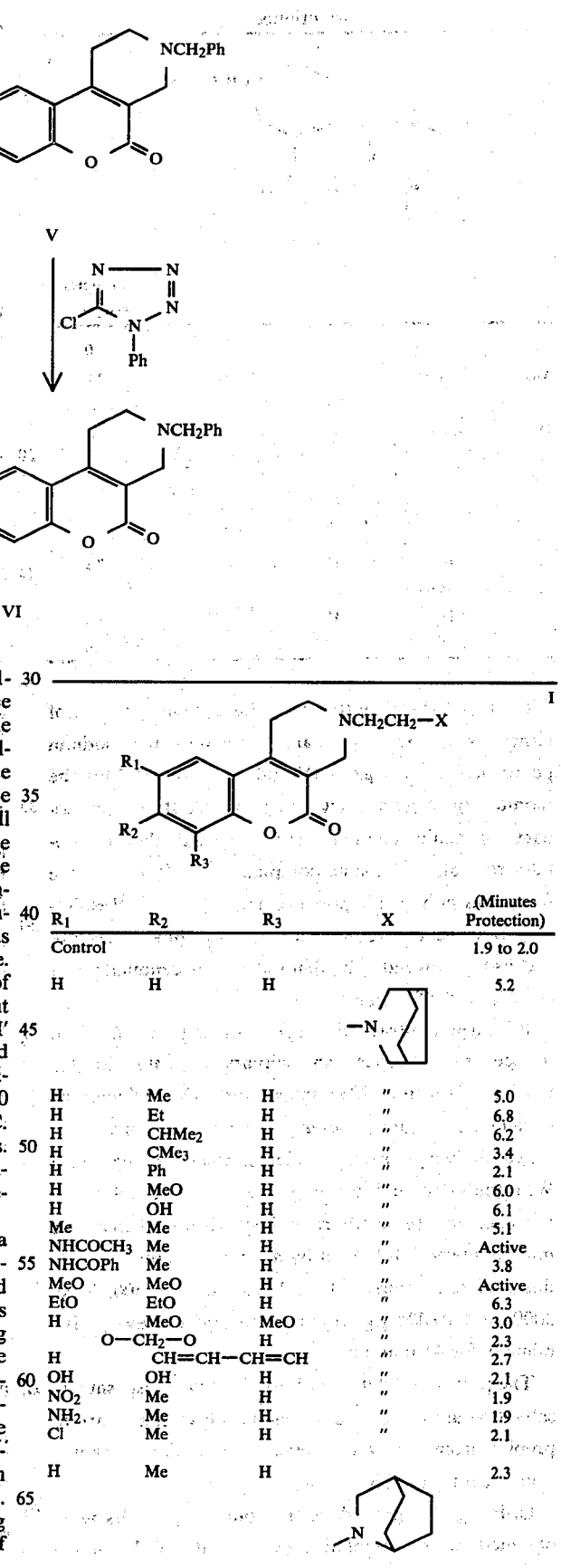

| $R_1$ | $R_2$ | $R_3$ | X | (Minutes Protection) |
|---|---|---|---|---|
| Control | | | | 1.9 to 2.0 |
| H | H | H | -N⟨ ⟩ | 5.2 |
| H | Me | H | " | 5.0 |
| H | Et | H | " | 6.8 |
| H | CHMe₂ | H | " | 6.2 |
| H | CMe₃ | H | " | 3.4 |
| H | Ph | H | " | 2.1 |
| H | MeO | H | " | 6.0 |
| H | OH | H | " | 6.1 |
| Me | Me | H | " | 5.1 |
| NHCOCH₃ | Me | H | " | Active |
| NHCOPh | Me | H | " | 3.8 |
| MeO | MeO | H | " | Active |
| EtO | EtO | H | " | 6.3 |
| H | MeO | MeO | " | 3.0 |
| O—CH₂—O | | H | " | 2.3 |
| H | CH=CH—CH=CH | | " | 2.7 |
| OH | OH | H | " | 2.1 |
| NO₂ | Me | H | " | 1.9 |
| NH₂ | Me | H | " | 1.9 |
| Cl | Me | H | " | 2.1 |
| H | Me | H | -N⟨bicyclic⟩ | 2.3 |

-continued

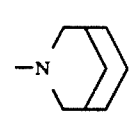

| $R_1$ | $R_2$ | $R_3$ | X | (Minutes Protection) |
|---|---|---|---|---|
| H | MeO | H | " | 10.0 |
| MeO | MeO | H | " | 7.6 |
| H | Me | H |  | 3.1 |
| H | MeO | H | " | 7.3 |
| MeO | MeO | H | " | 6.6 |
| H | H | H | " | 3.3 |
| Cl | Me | H | " | 2.6 |

In an additional testing procedure, mongrel dogs of either sex, 10.6 to 15.3 kg, are anesthetized with sodium pentobarbital, 30 mg/kg IV and then prepared for the monitoring of pulmonary mechanics. A Buxco pulmonary mechanics computer is used to calculate pulmonary resistance, dynamic compliance, and tidal volume from transpulmonary pressure and flow data. Respiratory rate, heart rate and mean arterial blood pressure are also monitored. The femoral vein is cannulated for the delivery of drugs.

Pilocarpine nitrate (0.2 mg/kg/hr) is than infused to induce a bronchospasm and salivary flow. Bunolol (0.5 mg/kg, IV) is given 30 minutes prior to the philocarpine to reduce the protein content, hence, the viscosity of the saliva. Salivary output is collected from a catheterized Wharton's duct at five minute intervals. After salivation has stabilized, three control collections are taken at five minute intervals followed by a series of cumulative IV doses of test compound (1, 3, 10, 30, 100, 300, 1000, 3000, and 10,000 µg/kg) that are injected every five minutes for 45 minutes.

The percent inhibition of both the bronchospasm and salivation are calculated for each dose with a return to prepilocarpine resistance levels or cessation of salivation equal to a 100% inhibition.

Utilizing this procedure the following results were obtained for representative compounds of the invention.

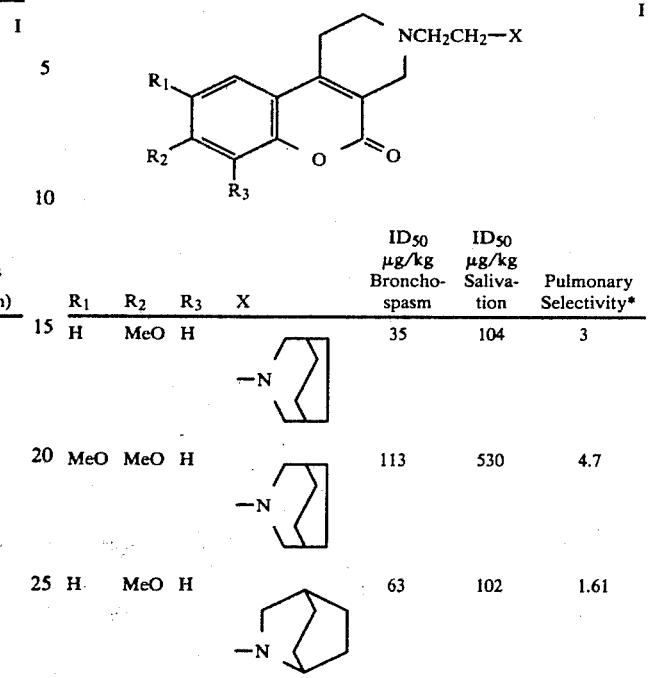

| $R_1$ | $R_2$ | $R_3$ | X | $ID_{50}$ µg/kg Bronchospasm | $ID_{50}$ µg/kg Salivation | Pulmonary Selectivity* |
|---|---|---|---|---|---|---|
| H | MeO | H |  | 35 | 104 | 3 |
| MeO | MeO | H |  | 113 | 530 | 4.7 |
| H | MeO | H |  | 63 | 102 | 1.61 |

*Pulmonary Selectivity = $\frac{ID_{50} \text{ Salivation}}{ID_{50} \text{ Bronchospasm}}$ where a value > 1 indicates the compound is more potent as a bronchodilator than as an antisecretory agent.

The compounds of the invention form pharmaceutically acceptable salts with organic and inorganic acids. Those skilled in the art will recognize that both mono and di salts may be prepared. Examples of suitable acids for salt formation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with a sufficient amount of the desired acid to produce either a mono or di salt in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups and alkoxy groups contemplated by the invention comprise both straight and branched carbon chains of from 1 to about 6 carbon atoms. Representative of such groups are methyl, ethyl, isopropyl, pentyl, 3-methylpentyl, methoxy, ethoxy, propoxy, 1-ethylbutoxy, pentoxy, and the like.

The term halogen is intended to include fluorine, chlorine, bromine, and iodine.

The term acylamino is intended to include groups of the general formula —NHCOA, wherein A represents either an alkyl group as defined above or phenyl.

The compounds of the invention can be prepared and administered in a wide variety of oral and parenteral dosage forms. Sprays for both oral and nasal administration are also contemplated. It will be obvious to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating asthma and bronchitis, the compounds utilized in the pharmaceutical method of this invention are administered at the initial dosage of about 0.5 mg to about 5 mg per kilogram daily. A daily dose range of about 2.0 mg to about 20 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the cirumstances is reached. For convenience, the total daily dosage may be divided and administered in portions during the day if desired.

The following nonlimiting examples illustrate the inventors' preferred methods for preparing the compounds of the invention.

EXAMPLE 1

3-[2-(3-Azabicyclo[3.2.2]non-3-yl)ethyl]-1,2,3,4-tetrahydro-8-methoxy-5H-[1]benzopyrano[3,4-c]pyridin-5-one, dihydrochloride A mixture of 8-methoxy-1,2,3,4-tetrahydro-5H-[1]benzopyrano[3,4-c]pyridin-5-one (2.31 g, 0.01 mole), 3-(2-chloroethyl)-3-azabicyclo(3.2.2)nonane hydrochloride (2.49 g, 0.01 mole) and triethylamine (3.03 g) in absolute ethanol (50 ml) is refluxed for 24 hours. The reaction mixture is filtered. Hydrogen chloride gas is bubbled through the filtrate. The product is filtered off, washed with ethanol and sucked dry. Recrystallization from methanol gave the product (2.34 g), mp 265°–270° C.

EXAMPLE 2

3-[2-(3-Azabicyclo[3.2.2]non-3-yl)ethyl]-8-(1,1-dimethylethyl)-1,2,3,4-tetrahydro-5H-[1]benzopyrano[3,4-c]pyridin-5-one, dihydrochloride Prepared by the method described for Example 1 from 8-(1,1-dimethylethyl)-1,2,3,4-tetrahydro-5H-[1]benzopyrano[3,4-c]-pyridin-5-one (4 g, 0.016 moles) and 3-(2-chloroethyl)-3-azabicyclo(3.2.2)nonane hydrochloride (3.6 g, 0.016 moles). Recrystallization from methanol gave the product (3.7 g), mp 312°–315° C.

EXAMPLE 3

3-(2-(3-Azabicyclo[3,2,2]non-3-yl)ethyl]-8-ethyl-1,2,3,4-tetrahydro-5H-benzopyrano[3,4-c]pyridin-5-one, dihydrochloride Prepared by the method described for Example 1 from 8-ethyl-1,2,3,4-tetrahydro-5H-[1]benzopyrano[3,4-c]pyridin-5-one (5.5 g, 0.024 moles) and 3-(2-chloroethyl)-3-azabicyclo(3.2.2)nonane hydrochloride (5.5 g, 0.025 moles). Recrystallization from ethanol gave the product (7.4 g), mp 295°–300° C.

EXAMPLE 4

3-[2-(3-Azabicyclo[3.2.2]non-3-yl)ethyl]-1,2,3,4-tetrahydro-8-phenyl-5H-[1]benzopyrano[3,4-c]pyridin-5-one, dihydrochloride Prepared by the method described for Example 1 from 8-phenyl-1,2,3,4-tetrahydro-5H-[1]benzopyrano[3,4-c]pyridin-5-one (5.54 g, 0.02 moles) and 3-(2-chloroethyl)-3-azabicyclo(3.2.2)nonane hydrochloride (4.48 g, 0.02 moles). Recrystallization from methanol gave the product (920 mg), mp 260°–265° C. (dec).

EXAMPLE 5

3-[2-(3-Azabicyclo[3.2.2]non-3-yl)ethyl]-1,2,3,4-tetrahydro-5H-[1]benzopyrano[3,4-c]pyridin-5-one Prepared by the method described for Example 1 from 1,2,3,4-tetrahydro-5H-[1]benzopyrano[3,4-c]pyridin-5-one (1.5 g, 0.007 moles), triethylamine (2.2 ml, 0.016 moles), and 3-(2-chloroethyl)-3-azabicyclo[3.2.2]nonane hydrochloride (1.7 g, 0.0076 moles). Recrystallization from ethanol gave the product (1.6 g) as the monohydrochloride, 5:1 hydrate, mp 267° C. (dec).

EXAMPLE 6

3-[2-(3-Azabicyclo[3.2.2]non-3-yl)ethyl]-1,2,3,4-tetrahydro-8-methyl-9-nitro-5H-[1]benzopyrano[3,4-c]pyridin-5-one Prepared by the method described for Example 1 from 1,2,3,4-tetrahydro-8-methyl-9-nitro-5H-[1]benzopyrano[3,4-c]pyridin-5-one (8.9 g, 0.034 moles), triethylamine (9.5 ml, 0.069 moles), and 3-(2-chloroethyl)-3-azabicyclo[3.2.2]nonane hydrochloride (7.7 g, 0.034 moles). The product was triturated with 10% aqueous potassium carbonate, filtered off, rinsed with water, and dried to afford the free base. Recrystallization from N,N-dimethylformamide gave the product (7.1 g), mp 187°–188° C.

EXAMPLE 7

3-[2-(3-Azabicyclo[3.2.2]non-3-yl)ethyl]-9-chloro-1,2,3,4-tetrahydro-8-methyl-5H-[1]benzopyrano[3,4-c]pyridin-5-one Prepared by the method described for Example 13 from 9-chloro-1,2,3,4-tetrahydro-8-methyl-5H-[1]benzopyrano[3,4-c]pyridin-5-one (2.0 g, 0.008 moles), 0.008 moles), triethylamine (2.3 ml, 0.017 moles), and 3-(2-chloroethyl)-3-azabicyclo[3.2.2]nonane hydrochloride (1.8 g, 0.008 moles). Recrystallization from ethanol gave the product (2.0 g) as the hemihydrochloride, mp 255° C. (dec).

EXAMPLE 8

3-[2-(3-Azabicyclo[3.2.2]non-3-yl)ethyl]-1,2,3,4-tetrahydro-8-methyl-5H-[1]benzopyrano[3,4-c]pyridin-5-one Prepared by the method described for Example 13 from 1,2,3,4-tetrahydro-8-methyl-5H-[1]benzopyrano[3,4-c]pyridin-5-one (2.0 g, 0.009 moles), triethylamine (3.1 ml, 0.022 moles), and 3-(2-chloroethyl-3-azabicyclo[3.2.2]nonane. Recrystallization from ethanol gave the product (1.7 g), mp 155°–157° C.

EXAMPLE 9

3-[2-(3-Azabicyclo[3.2.2]non-3-yl)ethyl]-1,2,3,4-tetrahydro-8-(1-methylethyl)-5H-[1]benzopyrano[3,4-c]pyridin-5-one dihydrochloride A mixture of 1,2,3,4-tetrahydro-8-(1-methylethyl)-5H-[1]benzopyrano[3,4-c]pyridin-5-one hydrochloride (6.5 g, 0.022 moles), triethylamine (8.4 g, 0.083 moles), and 3-(2-chloroethyl)-3-azabicyclo[3.2.2]nonane hydrochloride (5.4 g, 0.024 moles) in absolute ethanol (135 ml) is stirred at reflux under a nitrogen atmosphere for 24 hours. The reaction mixture is filtered while still hot, and the filtrate is treated with excess gaseous hydrogen chloride. Cooling yielded the crude product as the dihydrochloride, which is filtered and washed with cold acetone. Several recrystallizations from absolute ethanol yielded the final product (1.6 g) as the dihydrochloride, mp 273°–275° C.

EXAMPLE 10

3-[2-(3-Azabicyclo[3.2.2]non-3-yl)ethyl]-1,2,3,4-tetrahydro-5H-[1,3]benzodioxolo[5',6':5,6]pyrano[3,4-c]pyridin-5-one Prepared by the method described in Example 9 from 1,2,3,4-tetrahydro-5H-[1,3]benzodioxolo[5',6':5,6]pyrano[3,4-c]pyridin-5-one hydrochloride (4.8 g, 0.017 moles), triethylamine (3.8 g, 0.038 moles), and 3-(2-chloroethyl)-3-azabicyclo[3.2.2]nonane hydrochloride (4.2 g, 0.019 moles). The crude dihydrochloride obtained initially is converted to the free base by partitioning between dichloromethane and dilute aqueous ammonium hydroxide. Recrystallization from 2-methoxyethanol/water yielded the final product (0.62 g) as the free base, mp 208°–211° C.

EXAMPLE 11

3-[2-(3-Azabicyclo[3.2.2]non-3-yl)ethyl]-1,2,3,4-tetrahydro-7,8-dimethoxy-5H-[1]benzopyrano[3,4-c]pyridin-5-one dihydrochloride Prepared by the method described in Example 9 from 1,2,3,4-tetrahydro-7,8-dimethoxy-5H-[1]benzopyrano[3,4-c]pyridin-5-one hydrochloride (6.0 g, 0.020 moles), triethylamine (4.0 g, 0.040 moles), and 3-(2-chloroethyl)-3-azabicyclo[3.2.2]nonane hydrochloride (5.4 g, 0.024 moles). Recrystallization from 95% ethanol and then from methanol yielded the product (0.85 g) as the dihydrochloride, mp 255°–258° C.

EXAMPLE 12

3-[2-(3-Azabicyclo[3.2.2]non-3-yl)ethyl]-1,2,3,4-tetrahydro-8,9-dimethoxy-5H-[1]benzopyrano[3,4-c]pyridin-5-one dihydrochloride Prepared by the method described in Example 9 from 1,2,3,4-tetrahydro-8,9-dimethoxy-5H-[1]benzopyrano[3,4-c]pyridin-5-one (5.2 g, 0.020 moles), triethylamine (4.9 g, 0.048 moles), and 3-(2-chloroethyl)-3-azabicyclo[3.2.2]nonane hydrochloride (5.4 g, 0.024 moles). Recrystallization from methanol yielded the final product (3.3 g) as the dihydrochloride, mp 229°–234° C.

EXAMPLE 13

3-[2-(3-Azabicyclo[3.2.2]non-3-yl)ethyl]-1,2,3,4-tetrahydro-8,9-dimethyl-5H-[1]benzopyrano[3,4-c]pyridin-5-one A mixture of 1,2,3,4-tetrahydro-8,9-dimethyl-5H-[1]benzopyrano[3,4-c]pyridin-5-one (6.0 g, 0.026 moles), triethylamine (6.1 g, 0.060 moles), and 3-(2-chloroethyl)-3-azabicyclo[3.2.2]nonane hydrochloride (6.3 g, 0.028 moles) in absolute ethanol (150 ml) is stirred at reflux under a nitrogen atmosphere for 24 hours. The crude product precipitates as the free base as the reaction mixture is cooled slowly to room temperature. The product is filtered and recrystallized from absolute ethanol to yield the final product (4.6 g), mp 174°–175° C.

EXAMPLE 14

3-[2-(3-Azabicyclo[3.2.2]non-3-yl)ethyl]-1,2,3,4-tetrahydro-8,9,10-trimethoxy-5H-[1]benzopyrano[3,4-c]pyridin-5-one hydrochloride Prepared by the method described in Example 13 from 1,2,3,4-tetrahydro-8,9,10-trimethoxy-5H-[1]benzopyrano[3,4-c]pyridin-5-one hydrochloride (10.0 g, 0.031 moles), triethylamine (6.8 g, 0.067 moles), and 3-(2-chloroethyl)-3-azabicyclo[3.2.2]nonane hydrochloride (7.5 g, 0.034 moles). The crude product began to precipitate as the monohydrochloride shortly after reflux of the reaction mixture began. The product is filtered and recrystallized several times from 2-methoxyethanol/water to yield the final product (5.5 g) as the monohydrochloride, mp 241°-243° C.

EXAMPLE 15

2-[2-(3-Azabicyclo[3.2.2]non-3-yl)ethyl]-1,2,3,4-tetrahydro-12H-naphtho[2',1':5,6]pyrano[3,4-c]pyridin-12-one dihydrochloride Prepared by the method described in Example 9 from 1,2,3,4-tetrahydro-12H-naphtho[2',1':5,6]pyrano[3,4-c]pyridin-12-one (7.6 g, 0.037 moles), triethylamine (4.1 g, 0.040 moles), and 3-(2-chloroethyl)-3-azabicyclo[3.2.2]nonane hydrochloride (7.6 g, 0.034 moles). Several recrystallizations from dilute aqueous hydrochloric acid yielded the final product (2.7 g) as the dihydrochloride, mp 267°-270° C.

EXAMPLE 16

9-Amino-3-[2-(3-azabicyclo[3.2.2]non-3-yl)ethyl]-1,2,3,4-tetrahydro-8-methyl-5H-[1]benzopyrano[3,4-c]pyridin-5-one A solution of 3-[2-(3-azabicyclo[3.2.2]non-3-yl)ethyl]-1,2,3,4-tetrahydro-8-methyl-9-nitro-5H-[1]benzopyrano[3,4-c]pyridin-5-one (10.5 g, 0.026 moles) in N,N-dimethylformamide (300 ml) is hydrogenated at 50 psi at 24° C. in the presence of Raney Nickel until the required amount of hydrogen has been taken up. The catalyst is filtered off and rinsed with hot N,N-dimethylformamide until free of organic material. The filtrate is slightly concentrated and cooled to give the product. Recrystallization from ethanol gave the product (5.1 g), mp 142°-143° C.

EXAMPLE 17

N-{3-[2-(3-Azabicyclo[3.2.2]non-3-yl)ethyl]-1,2,3,4-tetrahydro-8-methyl-5-oxo-2H-[1]benzopyrano[3,4-c]pyridin-9-yl}-acetamide A solution of 9-amino-3-[2-(3-azabicyclo[3.2.2]non-3-yl)ethyl]-1,2,3,4-tetrahydro-8-methyl-5H-[1]benzopyrano[3,4-c]pyridin-5-one (1.8 g, 0.005 moles), pyridine (10 ml), and acetic anhydride (0.5 ml, 0.005 moles) is stirred overnight at room temperature. The mixture is poured into ice water (100 ml) and extracted with dichloromethane (3×40 ml). The combined extracts are washed with 0.5 M sodium bicarbonate, dried (magnesium sulfate), and evaporated under reduced pressure. Toluene (2×20 ml) is added to the residue, stirred, and evaporated, leaving a crystalline residue. Recrystallization from ethyl acetate, then ethanol, gave the product (0.3 g), mp 199°-200° C.

EXAMPLE 18

N-{3-[2-(3-Azabicyclo[3.2.2]non-3-yl)ethyl]-1,3,4,5-tetrahydro-8-methyl-5-oxo-2H-[1]benzopyrano[3,4-c]pyridin-9-yl}-benzamide A mixture of 9-amino-3-[2-(3-azabicyclo[3.2.2]non-3-yl)ethyl]-1,2,3,4-tetrahydro-8-methyl-5H-benzopyrano[3,4-c]pyridin-5-one (2.5 g, 0.007 moles), potassium carbonate (2.4 g, 0.017 moles), and benzoyl chloride (1.0 ml, 0.009 moles) is stirred in chloroform (50 ml) at room temperature. After 24 hours the mixture is poured into ice water. The layers are separated, and the aqueous phase is extracted with chloroform (2×60 ml). The combined organic extracts are washed with brine and dried (magnesium sulfate). The solvent is removed under reduced pressure to leave a syrup, which crystallized from ethyl acetate. Recrystallization gave the product (1.3 g), mp 174°-176° C.

EXAMPLE 19

3-[2-(3-Azabicyclo[3.2.2]non-3-yl)ethyl]-1,2,3,4-tetrahydro-8,9-dihydroxy-5H-[1]benzopyrano[3,4-c]pyridin-5-one dihydrobromide A solution of 3-[2-(3-azabicyclo[3.2.2]non-3-yl)ethyl]-1,2,3,4-tetrahydro-8,9-dimethoxy-5H-[1]benzopyrano[3,4-c]pyridin-5-one dihydrochloride (10.0 g, 0.020 moles) and 48% aqueous hydrobromic acid (100 ml) is stirred at reflux for 16 hours. The dihydrobromide product (10.7 g) is used as an intermediate without additional purification. A sample recrystallized from aqueous methanol/N,N-dimethylformamide had mp 270° C. (dec).

EXAMPLE 20

3-[2-(3-Azabicyclo[3.2.2]non-3-yl)ethyl]-1,2,3,4-tetrahydro-7,8-dihydroxy-5H-[1]benzopyrano[3,4-c]pyridin-5-one dihydrobromide Prepared by the method described in Example 19 from 3-[2-(3-azabicyclo[3.2.2]non-3-yl)ethyl]-1,2,3,4-tetrahydro-7,8-dimethoxy-5H-[1]benzopyrano[3,4-c]pyridin-5-one dihydrochloride (1.3 g, 0.0027 moles) and aqueous 48% hydrobromic acid (25 ml) plus acetic acid cosolvent (25 ml). After washing with a small amount of warm acetic acid, the final product (0.90 g) had mp 310°-313° C.

EXAMPLE 21

3-[2-(3-Azabicyclo[3.2.2]non-3-yl)ethyl]-1,2,3,4-tetrahydro-8,9-diethoxy-5H-[1]benzopyrano[3,4-c]pyridin-5-one A mixture 3-[2-(3-azabicyclo-[3.2.2]non-3-yl)ethyl]-1,2,3,4-tetrahydro-8,9-dihydroxy-5H-[1]benzopyrano[3,4-c]pyridin-5-one dihydrobromide (11.5 g, 0.020 moles), potassium carbonate (15.0 g, 0.11 moles), and diethyl sulfate (10.4 g, 0.067 moles) in 2.5 l of acetone is stirred at reflux for 21 hours. Additional diethyl sulfate (59 g, 0.38 moles) is added, and the mixture is heated for an additional 30 hours. The cooled mixture is filtered, and the filter cake is digested twice in hot acetone (500 ml) and refiltered. The combined filtrates are evaporated, and the residue is distributed between dichloromethane (1500 ml) and water (750 ml). The organic layer is separated, washed four times with 2.5% aqueous sodium hydroxide (750 ml), dried over sodium sulfate, and evaporated. The crude product was recrystallized twice as the free base from acetonitrile to yield the final product (5.4 g), mp 132°-134° C.

EXAMPLE 22

3-[2-(3-Azabicyclo[3.3.1]non-3-yl)ethyl]-1,2,3,4-tetrahydro-8-methyl-5H-[1]benzopyrano[3,4-c]pyridin-5-one Prepared by the method described for Example 13 from 1,2,3,4-tetrahydro-8-methyl-5H-[1]benzopyrano[3,4-c]pyridin-5-one (3.0 g, 0.014 moles), triethylamine (4.2 ml, 0.030 moles), and 3-(2-chloroethyl)-3-azabicyclo[3.3.1]nonane (3.3 g, 0.015 moles). The reflux time is 72 hours. Recrystallization from ethanol gave the product (3.6 g), mp 150°-152° C.

EXAMPLE 23

3-[2-(3-Azabicyclo[3.3.1]non-3-yl)ethyl]-1,2,3,4-tetrahydro-8-methoxy-5H-[1]benzopyrano[3,4-c]pyridin-5-one Prepared by the method described for Example 13 from 1,2,3,4-tetrahydro-8-methoxy-5H-[1]benzopyrano[3,4-c]pyridin-5-one (3.0 g, 0.013 moles), triethylamine (7.2 ml, 0.052 moles), and 3-(2-chloroethyl)-3-azabicyclo-[3.3.1]nonane hydrochloride (3.25 g, 0.015 moles). Recrystallization from ethanol gave the product (2.4 g), mp 102°-103° C.

EXAMPLE 24

3-[2-(3-Azabicyclo[3.3.1]non-3-yl)ethyl]-1,2,3,4-tetrahydro-8,9-dimethoxy-5H-[1]benzopyrano[3,4-c]pyridin-5-one Prepared by the method described for Example 13 from 1,2,3,4-tetrahydro-8,9-dimethoxy-5H-[1]benzopyrano[3,4-c]pyridin-5-one (3.0 g, 0.011 moles), triethylamine (6.4 ml, 0.046 moles), and 3-(2-chloroethyl)-3-azabicyclo[3.3.1]nonane hydrochloride (3.0 g, 0.013 moles). The reflux time is 96 hours. Recrystallization from ethanol gave the product (2.9 g), mp 122°-125° C.

EXAMPLE 25

3-[2-(3-Azabicyclo[3.3.1]non-3-yl)ethyl]-1,2,3,4-tetrahydro-5H-[1]benzopyrano[3,4-c]pyridin-5-one Prepared by the method described for Example 13 from 1,2,3,4-tetrahydro-5H-[1]benzopyrano[3,4-c]pyridin-5-one (0.8 g, 0.004 moles), triethylamine (1.3 ml, 0.009 moles), and 3-(2-chloroethyl)-3-azabicyclo[3.3.1]nonane hydrochloride (1.0 g, 0.0045 moles). The reflux time is 72 hours. The crude product is triturated in 10% aqueous potassium carbonate, filtered off, rinsed with water, and dried to give the product (0.5 g), mp 129°-130° C.

EXAMPLE 26

3-[2-(3-Azabicyclo[3.3.1]non-3-yl)-9-chloro-1,2,3,4-tetrahydro-8-methyl-5H-[1]benzopyrano[3,4-c]pyridin-5-one Prepared by the method described for Example 13 from 9-chloro-1,2,3,4-tetrahydro-8-methyl-5H-[1]benzopyrano[3,4-c]pyridin-5-one (1.2 g, 0.005 moles), triethylamine (1.4 ml, 0.010 moles), and 3-(2-chloroethyl)-3-azabicyclo[3.3.1]nonane hydrochloride (1.1 g, 0.005 moles). Recrystallization from methanol gave the product (1.2 g), mp 147°-149° C.

EXAMPLE 27

3-[2-(2-Azabicyclo[2.2.2]oct-2-yl)ethyl]-1,2,3,4-tetrahydro-8-methyl-5H-[1]benzopyrano[3,4-c]pyridin-5-one Prepared by the method described for Example 13 from 1,2,3,4-tetrahydro-8-methyl-5H-[1]benzopyrano[3,4-c]pyridin-5-one (3.0 g, 0.014 moles), triethylamine (4.1 ml, 0.030 moles), and 2-(2-chloroethyl)-2-azabicyclo[2.2.2]octane (3.0 g, 0.014 moles). The reflux time is 3 weeks. The product is obtained as the monohydrochloride. It is taken up in water, filtered, extracted with ethyl acetate, and precipitated as the free base by the addition of solid potassium carbonate. The precipitate is filtered off, rinsed with water, and dried to give the product (3.1 g), mp 113°-114° C.

EXAMPLE 28

3-[2-(2-Azabicyclo[2.2.2]oct-2-yl)ethyl]-1,2,3,4-tetrahydro-8-methoxy-5H-[1]benzopyrano[3,4-c]pyridin-5-one Prepared by the method described for Example 27 from 1,2,3,4-tetrahydro-8-methoxy-5H-[1]benzopyrano[3,4-c]pyridin-5-one (3.0 g, 0.013 moles), triethylamine (3.9 ml, 0.028 moles), and 2-(2-chloroethyl)-2-azabicyclo[2.2.2]octane hydrochloride (2.9 g, 0.014 moles). Reflux time is 3 weeks. The crude product is dissolved in water, extracted with ethyl acetate, precipitated by the addition of solid potassium carbonate, filtered off, rinsed with water, and dried to yield the final product (2.3 g), mp 112°-113° C.

EXAMPLE 29

3-[2-(2-Azabicyclo[2.2.2]oct-2-yl)ethyl]-1,2,3,4-tetrahydro-8,9-dimethoxy-5H-[1]benzopyrano[3,4-c]pyridine-5-one Prepared by the method described for Example 27 from 1,2,3,4-tetrahydro-8,9-dimethoxy-5H-[1]benzopyrano[3,4-c]pyridin-5-one (3.0 g, 0.011 moles), triethylamine (3.4 ml, 0.024 moles), and 3-(2-chloroethyl)-2-azabicyclo[2.2.2]octane hydrochloride (2.5 g, 0.012 moles). The product is dissolved in water, precipitated by the addition of 10% aqueous potassium carbonate, filtered off, rinsed with water, and dried. Recrystallization from ethyl acetate gave the product (1.4 g), mp 133°-135° C.

We claim:

1. A compound having the structural formula I

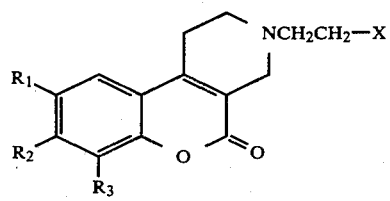

wherein $R_1$ is H, alkyl of from 1 to 6 carbon atoms, alkoxy of from about 1 to 6 carbon atoms, hydroxy, nitro, halo, amino, or $C_{1-4}$ alkanoylamine; $R_2$ is H, hydroxy, alkyl of from 1 to 6 carbon atoms, alkoxy of from 1 to 6 carbon atoms or phenyl; $R_3$ is H, or alkoxy of from 1 to 6 carbon atoms; $R_1$ and $R_2$ taken together are OCH$_2$O; $R_2$ and $R_3$ taken together are CH=CH—CH=CH; X is

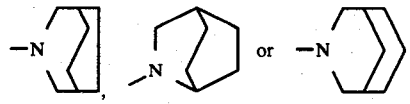

and the pharmaceutically acceptable salts thereof, provided that $R_1$ is not hydroxy when $R_2$ is $OC_2H_5$ and X is

2. The compounds defined in claim 1 wherein $R_3$ is H, and the pharmaceutically acceptable salts thereof.

3. The compounds defined in claim 1 wherein X is

and the pharmaceutically acceptable thereof.

4. The compound defined in claim 1 having the name 3-[2-(3-azabicyclo[3.2.2]non-3-yl)ethyl]-8-ethyl-1,2,3,4-tetrahydro-5H-[1]benzopyrano[3,4-c]pyridin-5-one and the pharmaceutically acceptable salts thereof.

5. The compound defined in claim 1 having the name 3-[2-(3-azabicyclo[3.2.2]non-3-yl)ethyl]-8-(1,1-dimethylethyl)-1,2,3,4-tetrahydro-5H-[1]benzopyrano[3,4-c]pyridin-5-one and the pharmaceutically acceptable salts thereof.

6. The compound defined in claim 1 having the name 3-[2-(3-azabicyclo[3.2.2]non-3-yl)ethyl]-1,2,3,4-tetrahydro-8-methoxy-5H-[1]benzopyrano[3,4-c]pyridin-5-one and the pharmaceutically acceptable salts thereof.

7. The compound defined in claim 1 having the name 3-[2-(3-azabicyclo[3.2.2]non-3-yl)ethyl-1,2,3,4-tetrahydro-8-hydroxy-5H-[1]benzopyrano[3,4-c]pyridin-5-one and the pharmaceutically acceptable salts thereof.

8. The compound defined in claim 1 having the name 3-[2-(3-azabicyclo[3.2.2]non-3-yl)ethyl]-1,2,3,4-tetrahydro-8,9-diethoxy-5H-[1]benzopyrano[3,4-c]pyridin-5-one and the pharmaceutically acceptable salts thereof.

9. The compound defined in claim 1 having the name 3-[2-(2-azabicyclo[2.2.2]oct-2-yl)ethyl]-1,2,3,4-tetrahydro-8-methoxy-5H-[1]benzopyrano[3,4-c]pyridin-5-one and the pharmaceutically acceptable salts thereof.

10. The compound defined in claim 1 having the name 3-[2-(2-azabicyclo[2.2.2]oct-2-yl)ethyl]1,2,3,4-tetrahydro-8,9-dimethoxy-5H-[1]benzopyrano[3,4]pyridin-5-one and the pharmaceutically acceptable salts thereof.

11. The compound defined in claim 1 having the name 3-[2-(3-azabicyclo[3.3.1]non-3-yl)ethyl]1,2,3,4-tetrahydro-8,9-dimethoxy-5H-[1]benzopyrano[3,4-c]pyridin-5-one and the pharmaceutically acceptable salts thereof.

12. The compound defined in claim 1 having the name 3-[2-(3-azabicyclo[3.3.1]non-3-yl)ethyl]-1,2,3,4-tetrahydro-8-methoxy-5H-[1]benzopyrano[3,4-c]pyridin-5-one and the pharmaceutically acceptable salts thereof.

13. The compound defined in claim 1 having the name 3-[2-(3-azabicyclo[3.2.2]non-3-yl)ethyl]-1,2,3,4-tetrahydro-8-,9-dimethoxy-5H-[1]benzopyrano[3,4-c]pyridin-5-one and the pharmaceutically acceptable salts thereof.

14. The compound defined in claim 1 having the name 3-[2-(3-azabicyclo[3.2.2]non-3-yl)ethyl]-1,2,3,4-tetrahydro-8,9-dimethyl-5H-[1]benzopyrano[3,4-c]pyridin-5-one and the pharmaceutically acceptable salts thereof.

15. The compound defined in claim 1 having the name 3-[2-(3-azabicyclo[3.2.2]non-3-yl)ethyl]-1,2,3,4-tetrahydro-8,-(1-methylethyl)-5H-[1]benzopyrano[3,4-c]pyridin-5-one and the pharmaceutically acceptable salts thereof.

16. The compound defined in claim 1 having the name N-{3-[2-(3-azabicyclo[3.2.2]non-3-yl)ethyl]-1,2,3,4-tetrahydro-8-methyl-5-oxo-2H-[1]benzopyrano[3,4-c]pyridin-9-yl}-acetamide and the pharmaceutically acceptable salts thereof.

17. The compound defined in claim 1 having the name 3-[2-(2-Azabicyclo[3.2.2]non-3-yl)ethyl]-1,2,3,4-tetrahydro-5H-[1]benzopyrano[3,4-c]pyridin-5-one and the pharmaceutically acceptable salts thereof.

18. A pharmaceutical composition consisting essentially of a compound defined in claim 1 in combination with a pharmaceutically acceptable carrier.

19. A method for treating asthma or bronchitis in a mammal in need of such treatment which comprises administering an effective amount of the pharmaceutically composition defined in claim 18 to said mammal.

* * * * *